United States Patent
Lam (10) Patent No.: US 9,983,185 B2
(45) Date of Patent: May 29, 2018

(54) CHEMOSENSING HYDROGEL FOR THE DETECTION OF BIOGENIC AMINES

(71) Applicant: City University of Hong Kong, Kowloon (HK)

(72) Inventor: Hon-Wah Lam, Kowloon (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 68 days.

(21) Appl. No.: 15/012,397

(22) Filed: Feb. 1, 2016

(65) Prior Publication Data
US 2017/0219549 A1 Aug. 3, 2017

(51) Int. Cl.
| G01N 33/00 | (2006.01) |
|---|---|
| G01N 33/12 | (2006.01) |
| C07F 15/02 | (2006.01) |
| G01N 21/78 | (2006.01) |
| G01N 31/22 | (2006.01) |

(52) U.S. Cl.
CPC ............. *G01N 33/12* (2013.01); *C07F 15/02* (2013.01); *G01N 21/783* (2013.01); *G01N 31/223* (2013.01); *G01N 33/0047* (2013.01); *G01N 33/0054* (2013.01)

(58) Field of Classification Search
CPC ...................................................... G01N 33/12
USPC ........................................................ 436/113
See application file for complete search history.

(56) References Cited

U.S. PATENT DOCUMENTS

| 4,963,324 A | 10/1990 | May |
| 7,332,343 B2 | 2/2008 | Anslyn et al. |
| 8,288,165 B2 | 10/2012 | Lam et al. |
| 2004/0072359 A1 | 4/2004 | Southard |

OTHER PUBLICATIONS

Rodrigue Lescouezec, Francesc Lloret, Miguel Julve, Jacqueline Vaissermann, and Michel Verdaguer, Inorg. Chem. 2002, 41, 818-826 (Year: 2002).*

Maynor, et al. A Food Freshness Sensor Using the Multistate Response from Analyte-Induced Aggregation of a Cross-Reactive Poly(thiophene); Organic Letters 2007, vol. 9, No. 17, 3217-3220.

Nelson, et al. Multi-layered analyses using directed partitioning to identify and discriminate between biogenic amines; Analyst 2007, 132, 1024-1030.

Herrera, et al. Photophysical and structural properties of cyanoruthenate complexes of hexaazatriphenylene; Journal of the American Chemical Society 2007,129,11491-11504.

(Continued)

*Primary Examiner* — Christine T Mui
*Assistant Examiner* — Emily R. Berkeley
(74) *Attorney, Agent, or Firm* — Amin, Turocy & Watson, LLP (57) ABSTRACT

A chemosensing hydrogel is provided that undergoes a colorimetric reaction in response to the detection of a biogenic amine vapor, such as a biogenic amine vapor that is a by-product resulting from food spoilage. In an embodiment, an apparatus for detection of biogenic amines, is provided that includes a hydrogel having a bimetallic iron (II)-iron(III) complex disposed within the hydrogel, wherein the hydrogel is configured to change from a first color to a second color in response to exposure to a biogenic amine.

20 Claims, 10 Drawing Sheets

(56) References Cited

OTHER PUBLICATIONS

Herrera, et al. Structural and Photophysical properties of coordination networks combining [Ru(Bpym)(CN)4]2- or [{Ru(CN)4}2(u-bpym)]4-anions (bpym=2,2'-bipyrimidine) with lanthanide(III) cations: sensitized near-infrared luminescence from Yb(III), Nd(III), and Er(III) following Ru-to-Lanthanide energy transfer; Inorganic Chemistry 2006, 45, 3895-3904.

Adams, et al. New members of the [Ru( diimine)(CN)4]2-family: structural, electrochemical and photophysical properties. DaltonTransactions 2005, 39-50.

\* cited by examiner

CHEMOSENSING HYDROGEL FOR THE DETECTION OF BIOGENIC AMINES

TECHNICAL FIELD

This application generally relates to detecting food spoilage and more particularly to a chemosensing hydrogel that detects a biogenic amine by-product resulting from food spoilage.

BACKGROUND

Spoilage of food, especially meats, is known to produce a suite of biogenic amines, such as histamine, cadaverine, putrescine, spermidine and tyramine, due to microbial-mediated degradation of proteins. The presence of excessive biogenic amines in food products indicates food decomposition that leads to poor quality and hygiene problems and may ultimately result in food poisoning. For example, histamine produced by spoiled meat is highly toxic and can cause scombroid food poisoning.

Currently, gas chromatography is the main analytical instrumentation for the quantitative determination of biogenic amines in food products. However, gas chromatography is expensive and tedious to use and maintain. Other qualitative and semi-quantitative screening tools use molecularly imprinted polymers and antibody-based immunoassays, however theses tools are not readily available to or easy to operable by the average consumer. Accordingly, there is a significant need for a mechanism to detect biogenic amines resulting from food spoilage that can produce an easily detectable result without the use of an external testing instrument.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which.

DETAILED DESCRIPTION

The various embodiments are described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and components are shown in block diagram form in order to facilitate describing the various embodiments.

By way of introduction, the subject matter described in this disclosure provides a low-cost, freestanding colorimetric chemosensing hydrogel material that gives a green to orange/red color change upon exposure to vapor of biogenic amines. The colorimetric detection is selective, sensitive and irreversible. No contact between the sensing hydrogel and the food item is needed, which eliminates the possibility of food contamination by chemicals. The chemosensing hydrogel includes a molecular bimetallic iron(II)-iron(III) complex with the two metal centres bridged by cyano-bridges. This bimetallic complex acts as a chemosensing ensemble that undergoes specific cleavage at the cyano-bridges upon contacting vapor of biogenic amines. The cleavage at the cyano-bridge results in a high-contrast color change from deep green to light orange.

The bimetallic complex can be incorporated into a hydrogel by soaking in an aqueous-organic solvent that develops into a gelatin-alginate hybrid hydrogel to produce the chemosensing hydrogel material. The chemosensing hydrogel is stable over long periods of storage time (e.g., at least 30 days) at ambient conditions. Accordingly, the subject chemosensing hydrogel material can serve as an excellent low cost food quality sensor for pre-packaged food products, especially meat and fish products.

In an embodiment, a chemical complex for detection of biogenic amines is provided that has a chemical structure of Structure I:

Structure I

Structure I is an example bimetallic iron(II)-iron(III) chemical complex. A solution including the chemical complex having structure I is configured to change from a first color to a second color in response to exposure to a biogenic amine. For example, the solution can include an aqueous solution including the chemical complex dissolved in water or a polar organic solvent. The biogenic amine can include but is not limited to histamine, putrescine, spermidine, ammonia or tyramine.

In another embodiment, an apparatus for detection of biogenic amines, is provided that includes a hydrogel having a bimetallic iron(II)-iron(III) complex disposed within the hydrogel. The hydrogel is configured to change from a first color to a second color in response to exposure to a biogenic amine. In particular, the hydrogel is configured to change from the first color to the second color in response to exposure to a biogenic amine vapor. Accordingly, the hydrogel need not make physical contact with a product (e.g., a spoiled meat or fish food product) that generates the biogenic amine. In an aspect, the bimetallic iron(II)-iron(III) complex has a chemical structure of Structure I above.

In yet another embodiment, a package for the containment of food is provided that includes a hydrogel and a bimetallic iron(II)-iron(III) complex disposed within the hydrogel. The hydrogel is configured to change from a first color to a second color in response to exposure to a biogenic amine generated by the food product. For example, the hydrogel can be configured to change from a green color to an orange or red color in response to exposure to a vapor including a biogenic amine that is generated by the food product in response to spoilage of the food product (e.g., wherein the food product includes meat or fish). In an aspect, the hydrogel is configured to change from the first color to the second color in response to exposure to the biogenic amine, even in the presence of moisture.

Figure 1A:
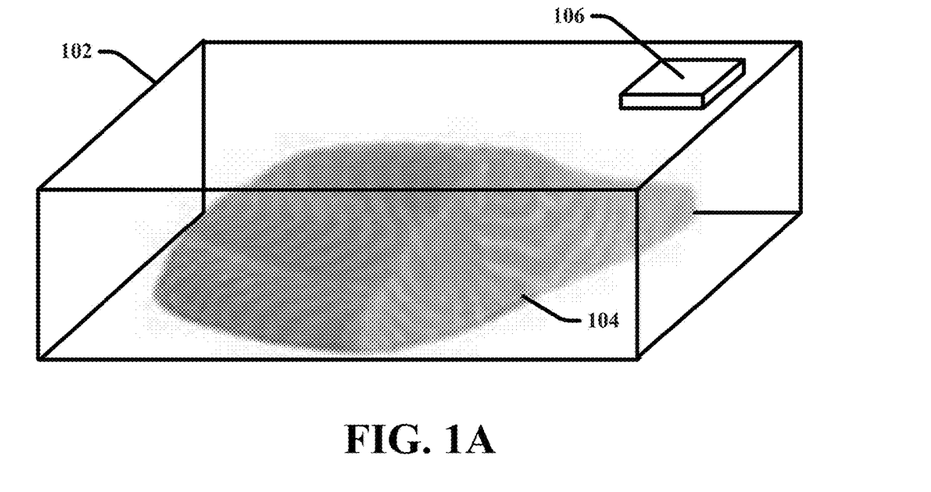
FIGS. 1A and 1B present an example food containment apparatus that includes a chemosensing hydrogel configured to generate a colorimetric reaction in response to detection of biogenic amines in accordance with various aspects and embodiments described herein.
Figure 1B:
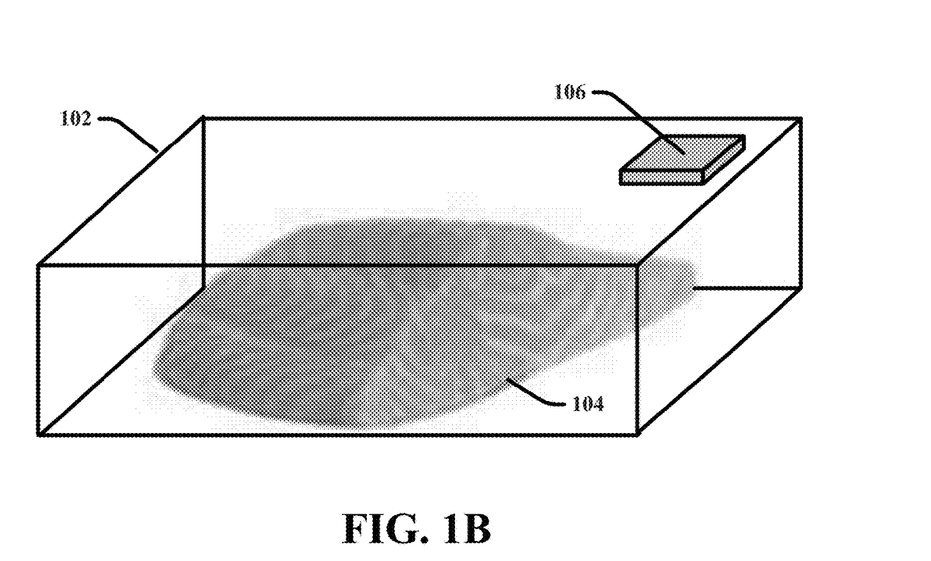

With reference now to FIGS. 1A and 1B, presented is an example food containment apparatus 102 that includes a chemosensing hydrogel 106 configured to generate a colorimetric reaction in response to exposure to biogenic amines, in accordance with various aspects and embodiments described herein. In particular, the chemosensing hydrogel 106 is configured to change color in response to exposure to one or more biogenic amines. Spoilage of food, especially meat and fish, is known to produce a suite of biogenic amines, such as histamine, cadaverine, putrescine, spermidine and tyramine, due to microbial-mediated degradation of proteins. The presence of excessive biogenic amines in food products indicates food decomposition that leads to poor quality and hygiene problems and may ultimately result in food poisoning. Accordingly, chemosensing hydrogel 106 can be used to detect spoilage of food.

For example, the food containment apparatuses of FIGS. 1A and 1B include a piece of raw fish 104 is contained therein. The chemosensing hydrogel 106 in FIGS. 1A and 1B is depicted in different colors to provide a visible indication of an amount of spoilage/decomposition of the raw fish 104. For example, the first color of the chemosensing hydrogel 106 in FIG. 1A can indicate the fish is not spoiled while the second color of the chemosensing hydrogel 106 in FIG. 1B can indicate the fish is spoiled.

The ability of the chemosensing hydrogel 106 to provide a colorimetric reaction in response to exposure to biogenic amines is based on a novel iron(II)-iron(III) bimetallic coordination complex incorporated into the hydrogel. In one or more embodiments, this iron(II)-iron(III) complex has the chemical structure of Structure I above and/or the chemical formula $[Fe^{II}(bpy)(CN)_4]_2-[Fe^{III}(H_2O)_6Cl]_2$, where bpy=bipyridine. Chemical Structure I has two metal centres bridged by cyano-bridges. When an aqueous solution including an iron(II)-iron(III) complex having chemical Structure I (or a similar structure) is exposed to a biogenic amine such as histamine, cadaverine, putrescine, spermidine and/or tyramine, the iron(II)-iron(III) complex undergoes specific cleavage at the cyano-bridges. This results in a high-contrast color change from deep green to light red/orange color. In some embodiments, the iron(II)-iron(III) complex may also be incorporated into a gaseous or solid solution.

The reaction between the biogenic amine and the iron(II)-iron(III) complex can occur when the biogenic amine is in vapor form (as well as when the biogenic amine is in an aqueous form). Accordingly, a solution (e.g., an aqueous solution) including the iron(II)-iron(III) complex is capable of producing a colorimetric reaction result that is visible to the naked eye when exposed to biogenic amines in ambient air. Thus a solution including the iron(II)-iron(III) complex is highly suitable for food quality and safety surveillance as the food samples are not required to make any physical contact with the chemosensing solution. This eliminates any possibility of food products being contaminated by chemicals.

In various embodiments, the iron(II)-iron(III) complex is synthesized from $K_2[Fe^{II}(bpy)(CN)_4]$ (where bpy=bipyridine) and anhydrous $FeCl_3$. For example, a solution including an iron(II)-iron(III) can be synthesized from $K_2[Fe^{II}(bpy)(CN)_4]$ and anhydrous $FeCl_3$ in 10% aqueous dimethyl sulfoxide (DMSO) at room temperature for about 60 minutes (Yield: 80%; IR (KBr): $v_{C\equiv N}$=2057 and 2071 cm$^{-1}$; ESI-MS (+ve mode): m/z 1015.4{H$^+$.[Fe$^{II}$(bpy)(CN)$_4$]$_2$—[Fe$^{III}$(H$_2$O)$_6$Cl]$_2$}).

The iron(II)-iron(III) complex can be incorporated into a hydrogel form in using various suitable techniques. A hydrogel is a highly porous three dimensional matrix assembled from hydrophilic components (i.e., components that are miscible with water and other polar solvents). This gives the resultant matrix the capability to trap water and other polar solvents, as well as chemical components that are dissolved in the solvents. In accordance with various embodiments of the subject disclosure, an aqueous solution including the molecular bimetallic iron(II)-iron(III) chemosensing complex is incorporated into a gelatin-chitosan hydrogel matrix. Inside the hydrogel matrix, the bimetallic iron(II)-iron(III) chemical complex exists in dissolved state. Accordingly, the hydrogel matrix provides the environment for bond cleavage of the iron(II)-iron(III) complex and the corresponding colormetric reaction in response to exposure to biogenic amines.

In one implementation, to produce the chemosensing hydrogel 106, an aqueous solution including the iron(II)-iron(III) complex is soaked with a gelatin-alginate hybrid hydrogel for a suitable amount of time (e.g., about one hour to about ten hours) to allow for incorporation of a desired amount of the iron(II)-iron(III) complex into the hydrogel. In an aspect, the gelatin-alginate hybrid hydrogel is obtained from an aqueous mixture of 1% sodium alginate and 10% gelatin in the presence of 0.2 M calcium chloride. However, other suitable gelatin or alginate hydrogel mixtures can be used.

For example, soaking a gelatin-alginate hydrogel composed of 1% sodium alginate, 10% gelatin and 0.2 M calcium chloride in a 0.1 mM DMSO solution of the iron(II)-iron(III) complex overnight results in incorporation of the iron(II)-iron(III) complex into the hydrogel. The resultant chemosensing hydrogel is deep green in color and can be stored out of any solvent in sealed containers for at least one month under ambient conditions without observable change or deterioration of chemosensing properties. When the hydrogel is exposed to the vapor of one or more biogenic amines, the hydrogel color changes from the deep green color to a red/orange color.

For example, an experiment conducted to ascertain the biogenic amine sensing capabilities of a 1.0 mm thickness chemosensing hydrogel (e.g., chemosensing hydrogel 106) obtained via the mechanism described above involved sealing the chemosensing hydrogel with a fresh whole fish obtained from wet market in a plastic bag for 10 hours at room temperature (e.g., about 21-25° C.). The chemosensing hydrogel was initially a dark green color. After the 10 hour period at room temperature, the chemosensing hydrogel had a dark red/orange color. This change in color of the chemosensing hydrogel is attributed to the generation of biogenic amines by the fish over time due to the microbial-mediated degradation of the fish proteins.

Real-time monitoring of the colorimetric responses of the chemosensing hydrogel has also been carried out using small pieces of the hydrogel (e.g., having a dimension of 1.0 cm×1.0 cm and a thickness of 1.0 mm). Time lap video-clips of the color change induced by fish meat and pork at kept room temperature (e.g., about 21-25° C.), and kept over an ice bath (e.g., about 10° C.) were recorded. The video clips revealed that the subject chemosensing hydrogel (prepared via the mechanism described above) required less than 24 hours to change color completely from an initial green to red/orange. When the fish and pork were stored at low-temperature over the ice bath, the chemosensing hydrogel did not change its color. This indicates that the color change of the chemosensing hydrogel was brought about the spoilage of the meat. In addition, the subject experiment also indicates that the functioning of the chemosensing hydrogel is not interfered by moisture from the food products. This is rather important as many chemosensors for amine-type analytes in the literature have the common problem of being interfered by water vapor in the real-world working conditions.

The color of the chemosensing hydrogel 106 gradually shifts from the initial green color to the red/orange color as the concentration of biogenic amine levels increase. Thus, a specific color of the chemosensing hydrogel 106 at any point in time can be directly correlated to an amount of biogenic amines included in a food product (e.g., the raw fish 104). Accordingly, the chemosensing hydrogel 106 can be configured (e.g., based on concentration of iron(II)-iron(III) complex in the hydrogel, and other additives to the hydrogel) to exhibit specific color properties based on different amounts of biogenic amines included in a food product to which the chemosensing hydrogel 106 is exposed.

The concentration of iron(II)-iron(III) complex included in the chemosensing hydrogel 106 can also be adapted based an amount of biogenic amine vapor production associated with a spoiled food product for which the hydrogel is being used to monitor. For example, the CODEX international food safety standard for histamine in fish and meat is 100 ppm (maximum average level). According to this example, the chemosensing hydrogel 106 can be loaded with a predetermined amount of iron(II)-iron(III) complex such that upon exposure to more than 100 ppm of histamine, the chemosensing hydrogel 106 has a distinct and predetermined color property. The greater the amount of iron(II)-iron(III) complex included in the hydrogel, the greater amount of biogenic amine concentration required to react with the hydrogel to generate a specific colorimetric reaction. In an aspect, chemosensing hydrogel 106 includes a 0.25 mM concentration of iron(II)-iron(III). In another aspect, chemosensing hydrogel 106 includes a 0.50 mM concentration of iron(II)-iron(III). Still in yet another aspect, chemosensing hydrogel 106 includes a 1.00 mM concentration of iron(II)-iron(III).

The size, shape and thickness of the chemosensing hydrogel 106 can vary. In an aspect, the chemosensing hydrogel 106 has a thickness of about 0.5 mm to about 5.0 mm. In another aspect, the chemosensing hydrogel 106 has a thickness of about 1.0 mm.

It should be appreciated that the disclosed iron(II)-iron (III) complex for the detection of biogenic amines is not limited to the incorporation into a hydrogel having the properties specified above. For example, various other aqueous (and potentially gaseous and solid) solutions, matrices, mixtures, dispersions, etc. can be formed with the subject iron iron(II)-iron(III) complex to facilitate the detection of biogenic amines.

In one embodiment, as exemplified in FIGS. 1A and 1B, the subject chemosensing hydrogel 106 can be integrated with a food containment apparatus 102. For example, the chemosensing hydrogel 106 can be incorporated into various types of containers that are used to package fish and meats. The size, shape, geometry and material of the containers can vary. For example, as depicted in FIGS. 1A and 1B, the container can include a substantially rectangular plastic dish with a clear lid. In another example, the container can include a flexible plastic bag configured to seal food products contained therein.

The location of the chemosensing hydrogel on or within the food containment apparatus 102 can also vary. In an exemplary embodiment, the chemosensing hydrogel 106 is located inside the container when sealed and positioned within the container such that it does not physically contact or touch the food product contained or to be contained therein. For example, as depicted in FIGS. 1A and 1B, the chemosensing hydrogel 106 can be located on an underside of a clear lid of the food containment apparatus 102 such that the color of the chemosensing hydrogel can be seen through the clear lid and the chemosensing hydrogel 106 does not touch the food product. In another example, the food containment apparatus 102 can include a slot or structure into which the chemosensing hydrogel is inserted. The structure can be configured to keep the chemosensing hydrogel physically separated from the food product while also allowing vapor generated by the food product to contact the chemosensing hydrogel (e.g., via one or more slits or holes in the structure).

In some embodiments, the food containment apparatus 102 can also include a color indicator strip (not shown) on an external area of the food containment apparatus. The color indicator strip can provide consumers with a chart that correlates different possible colors of the chemosensing hydrogel 106 with degrees of food spoilage. For example, a color indicator strip can be located on an external area of the container near the chemo sensing hydrogel 106 and include a dark green color, a light green color, a light red color and a dark red color. Each of these respective colors can be associated with instructions identifying an amount of food spoilage/biogenic amine level indicated by the color and an indication of safely level associated with consuming the product when the respective colors are demonstrated.

Figure 2:
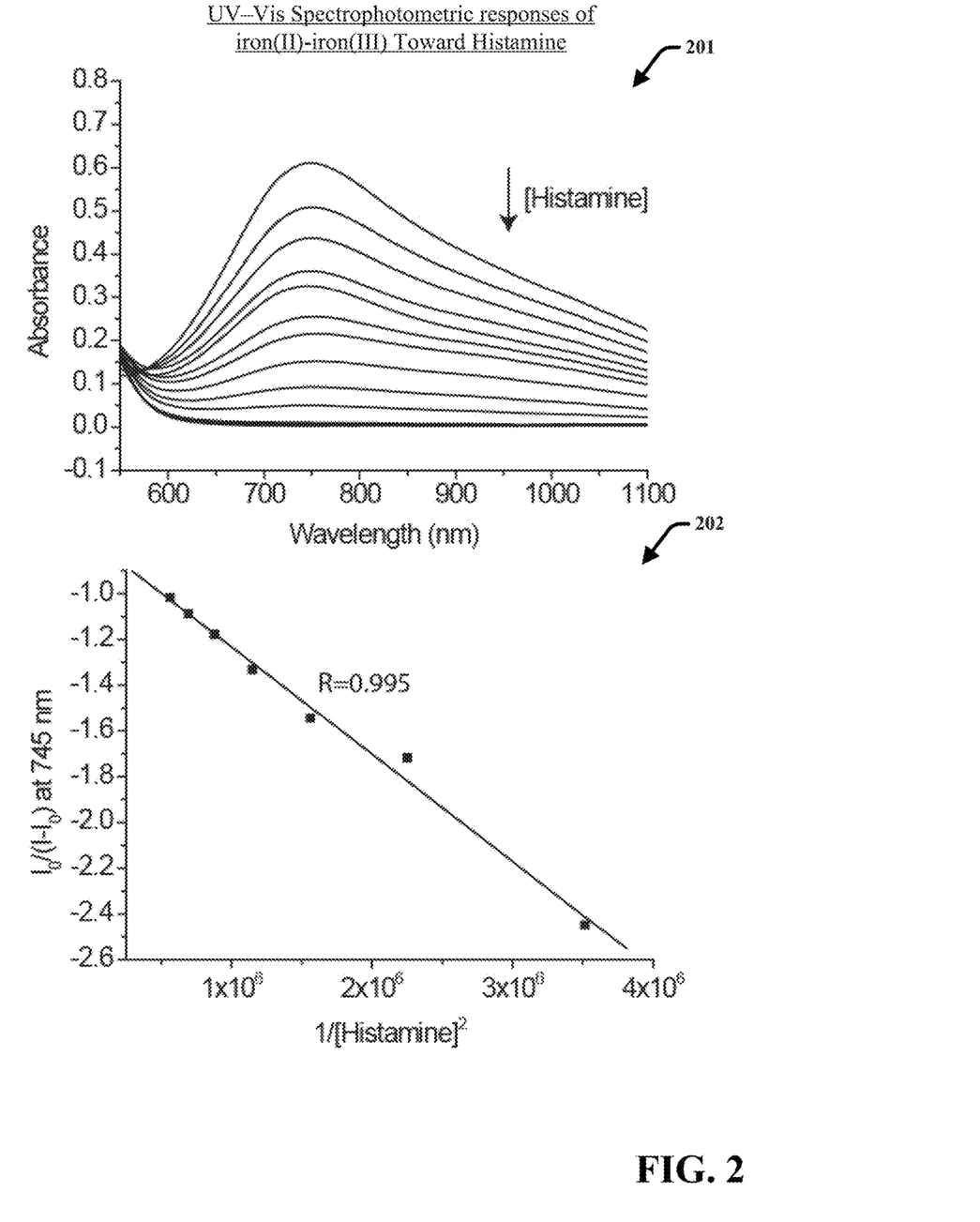
FIG. 2 provides graphical representations of the UV-Vis spectrophotometric responses of a bimetallic iron(II)-iron(III) complex toward histamine in accordance with various aspects and embodiments described herein.
Figure 3:
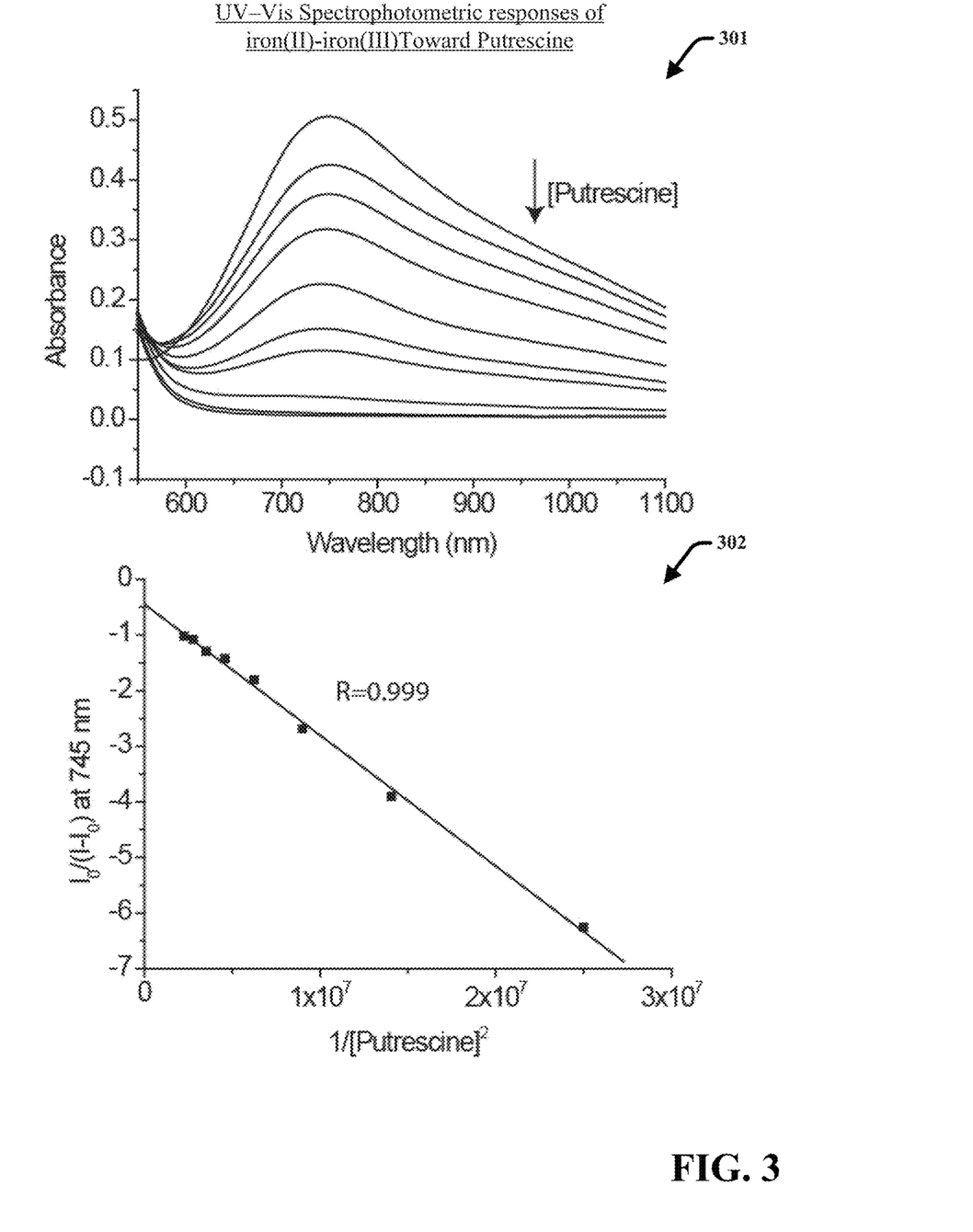
FIG. 3 provides graphical representations of the UV-Vis spectrophotometric responses of a bimetallic iron(II)-iron(III) complex toward putrescine in accordance with various aspects and embodiments described herein.
Figure 4:
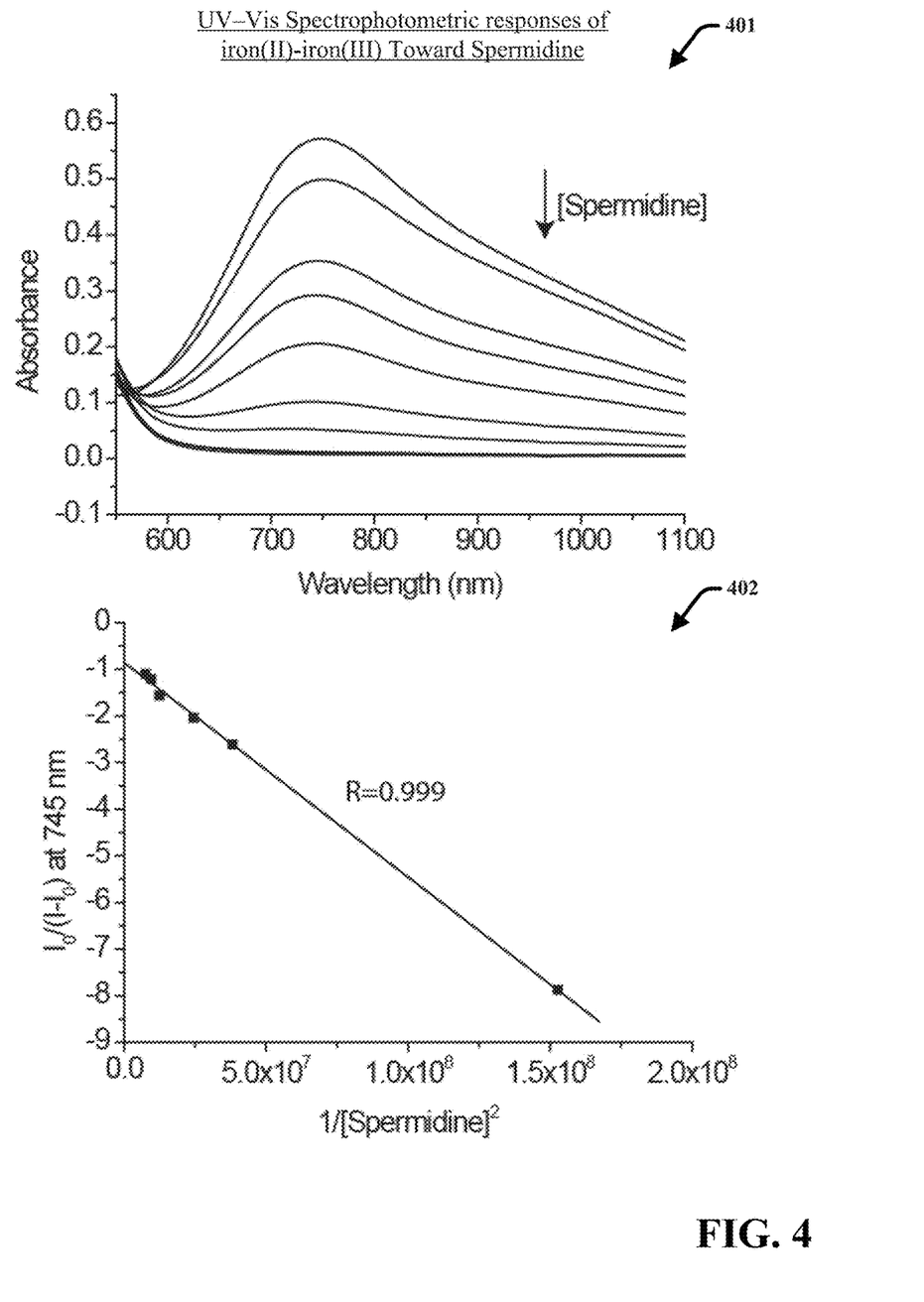
FIG. 4 provides graphical representations of the UV-Vis spectrophotometric responses of a bimetallic iron(II)-iron(III) complex toward spermidine in accordance with various aspects and embodiments described herein.
Figure 5:
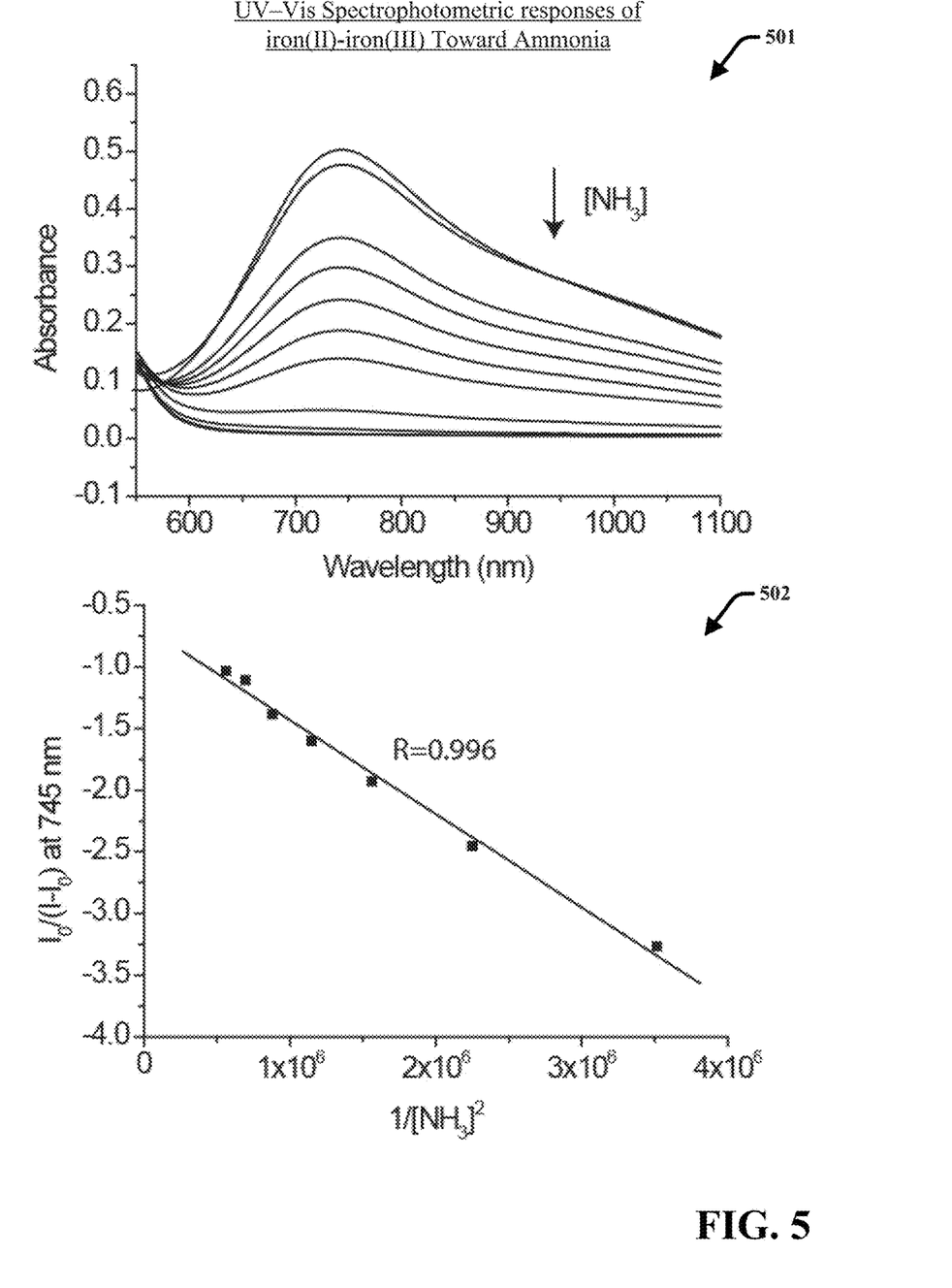
FIG. 5 provides graphical representations of the UV-Vis spectrophotometric responses of a bimetallic iron(II)-iron(III) complex toward ammonia in accordance with various aspects and embodiments described herein.

FIGS. 2-5 present graphical representations of the UV-vis spectrophotometric responses of a subject bimetallic iron(II)-iron(III) complex towards different biogenic amines. FIG. 2 presents graphical representations 201 and 202 of the UV-Vis spectrophotometric responses of the bimetallic iron(II)-iron(III) complex toward histamine. FIG. 3 presents graphical representations 301 and 302 of the UV-Vis spectrophotometric responses of the bimetallic iron(II)-iron(III) complex toward putrescine. FIG. 4 presents graphical representations 401 and 402 of the UV-Vis spectrophotometric responses of the bimetallic iron(II)-iron(III) complex toward spermidine, and FIG. 5 presents graphical representations 501 and 502 of the UV-Vis spectrophotometric responses of the bimetallic iron(II)-iron(III) complex toward ammonia.

In accordance with FIGS. 2-5, an aqueous solution containing the subject iron(II)-iron(III) complex (e.g., having Structure I) was synthesized from $K_2[Fe^{II}(bpy)(CN)_4]$ (where bpy=bipyridine) and anhydrous $FeCl_3$ in 10% aqueous DMSO at room temperature for about 60 minutes, (Yield: 80%; IR (KBr): $v_{C\equiv N}$=2057 and 2071 cm$^{-1}$; ESI-MS (+ve mode): m/z 1015.4{$H^+$·[$Fe^{II}$(bpy)(CN)$_4$]$_2$—[$Fe^{III}$(H$_2$O)$_6$Cl]$_2$}). The aqueous solution was then used to perform UV-vis spectrophotometric titrations of solutions of iron(II)-iron(III) (1.67×10$^{-4}$ M) by histamine, putrescine, spermidine (0 to 1.67×10$^{-3}$ M) and ammonia (0 to 1.38× 10$^{-5}$ M) in a 9:1 ratio of water/DMSO mixture. Observed absorbance of the resultant mixtures at 745 nm, after equilibrium had been reached between the receptor and substrate, was measured. The spectroscopic responses were fitted to a Benesi-Hildebrand 1:2 receptor-substrate interaction model:

$$\frac{A_O}{A-A_O} = \left(\frac{\varepsilon_o}{\varepsilon_o-\varepsilon}\right)^2 \left(\frac{1}{K_{Overall}[\text{substrate}]^2} + 1\right)$$

where $A_O$ and $A$ are the absorbance of the chromogenic reagent in the absence and presence of the substrate, and $\varepsilon_o$ and $\varepsilon$ are the corresponding molar absorption coefficients of the chromogenic reagent in the absence and presence of the substrate. Formation constants ($K_{overall}$) were estimated from the ratio between the y-intercept and the slope of straight lines obtained by plotting $A_O/(A-A_O)$ vs. 1/[substrate]$^2$. The best fitted plots reveal log $K_{overall}$ of 3.11±0.04, 3.14±0.02, 3.63±0.02 and 3.00±0.06 for histamine, putrescine, spermidine and ammonia respectively.

Figure 6:
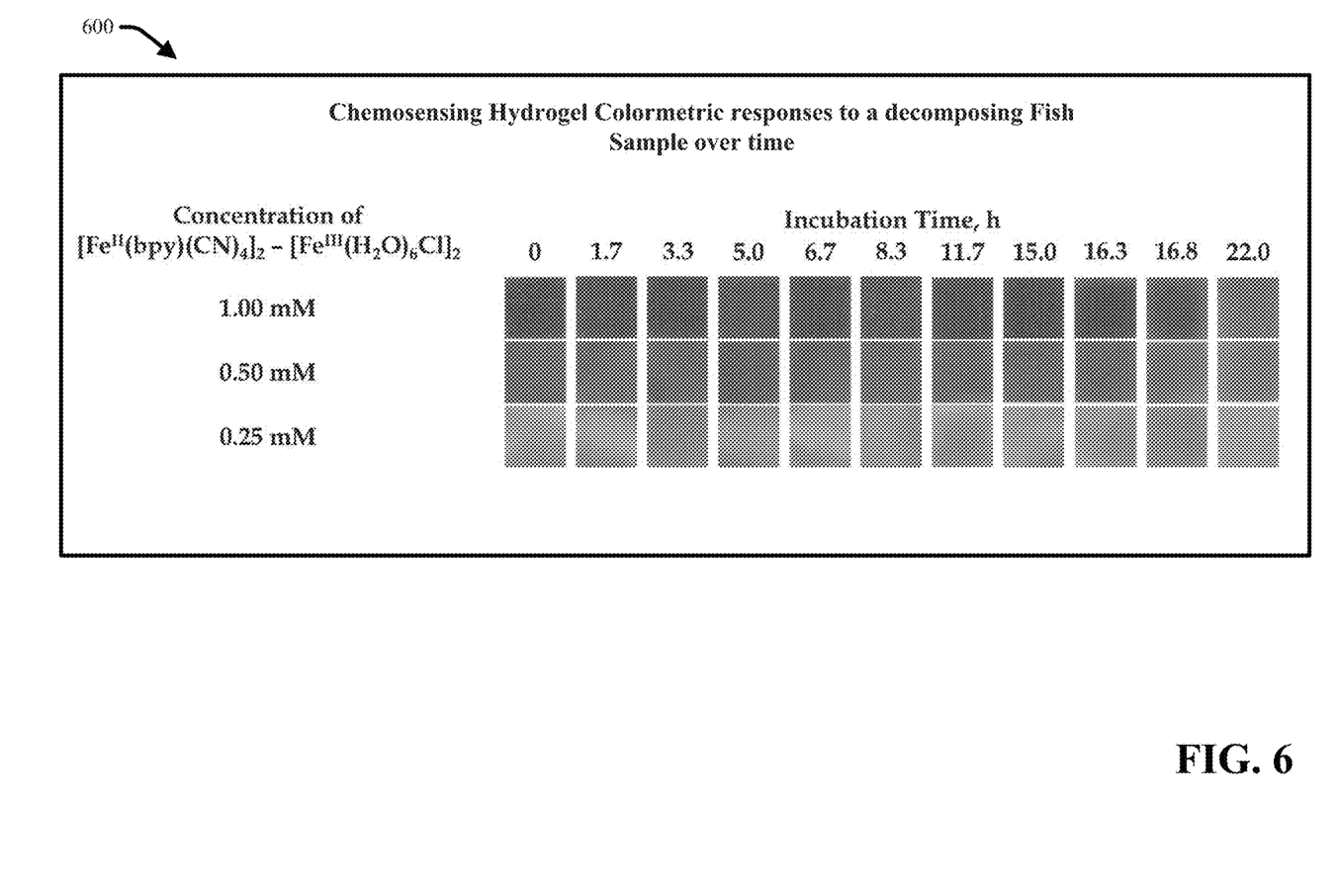
FIG. 6 presents a chart comparing the colorimetric responses of a chemosensing hydrogel to a decomposing fish sample over time in accordance with various aspects and embodiments described herein.
Figure 7:
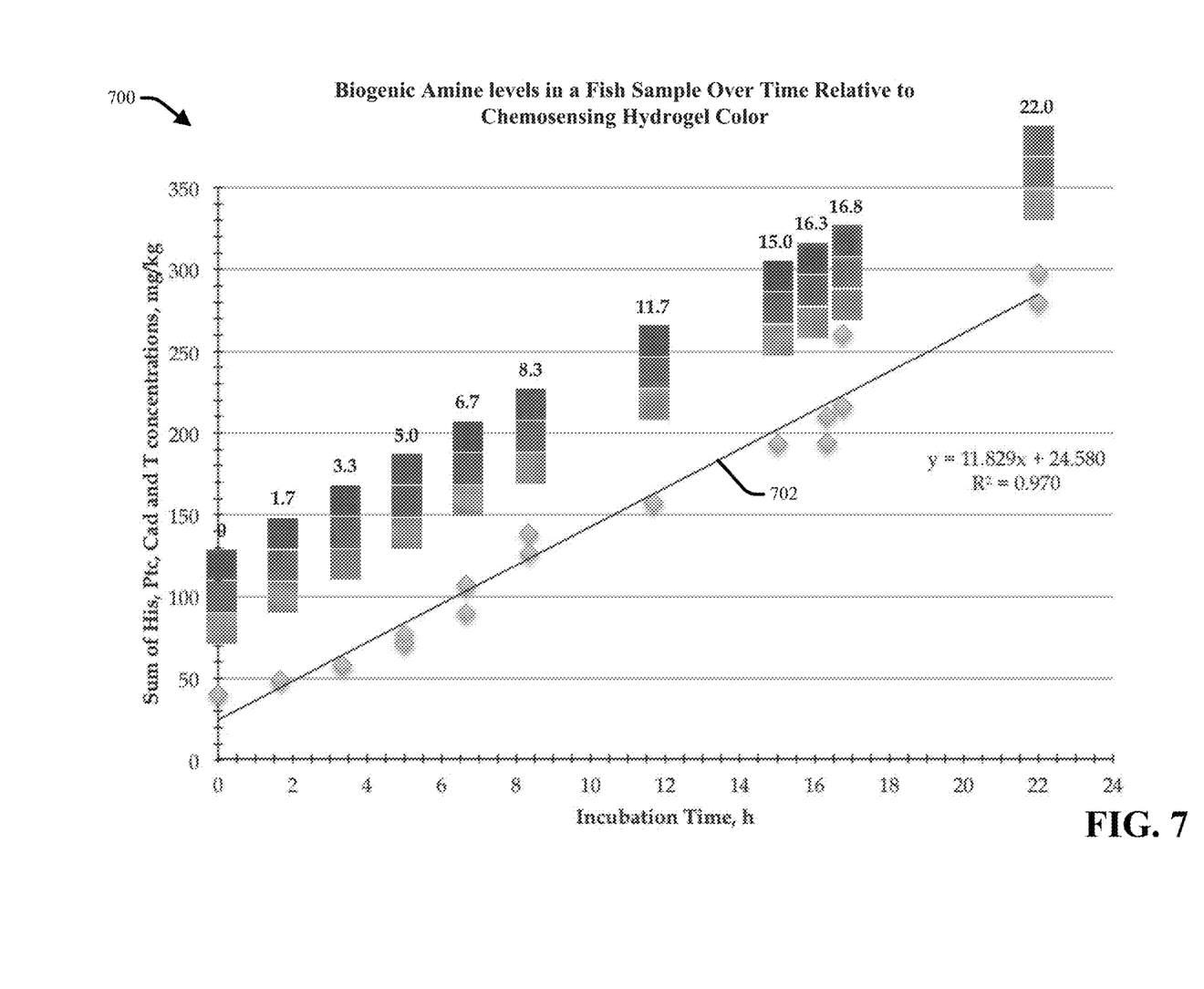
FIG. 7 provides a graphical representation of biogenic amine levels in a fish sample over time relative to a colorimetric response generated by a chemosensing hydrogel in accordance with various aspects and embodiments described herein.

FIGS. 6 and 7 present the colorimetric results of another experiment assessing the chemosensing abilities of the subject chemosensing hydrogel against biogenic amines in association with decomposition of a fish sample. FIG. 6 presents a chart 600 comparing the colorimetric responses of the chemosensing hydrogel to the decomposing fish sample over time, and FIG. 7 provides a graphical representation 700 of biogenic amine levels in the fish sample over time relative to a colorimetric responses generated by the chemosensing hydrogel.

In accordance with the results depicted in FIGS. 6 and 7, a series of chemosensing hydrogels (e.g., gelatin-alginate) with different loading of concentrations (e.g., 0.25 mM, 0.5 mM, and 1.0 mM, respectively) of the subject iron(II)-iron(III) complex were incubated with homogenized fish meat (35.0 g each of nemipterus virgatus) at 30° C. At fixed time intervals 0, 1.7, 3.3, 5.0, 6.7, 8.3, 11.7, 15.0, 16.3, 16.8 and 22.0 hours, concentrations of various biogenic amines (histamine, cadaverine, putrescine and tyramine) in the fish meat were determined by gas chromatography-mass spectrometry (GC-MS), and the color of the hydrogel was recorded by digital photography.

An induction period of about 4-5 hours was observed before the spoilage of the fish meat started to emit histamine, cadaverine and putrescine. On the other hand, there was no induction period for tyramine emission, but it started to level off after about 4-5 hours.

The graphical representation 700 in FIG. 7 plots the sum emission of the respective biogenic amines histamine, cadaverine and putrescine and tyramine at the respective time intervals over a 22 hour period. Their overall emission rate becomes rather linear for the 22 hour period (as indicated by line 702). As seen in FIGS. 6 and 7, the color change of the chemosensing hydrogel is subtler. For the lightest loaded hydrogel (at 0.25 mM of iron(II)-iron(III)), a noticeable color change occurred at about 12 hours when the overall level of biogenic amines in the fish meat accumulated to slightly above 200 ppm. For the heavier loaded hydrogels (at from 0.5 and 1.0 mM iron(II)-iron(III), a color change occurred later at about 16 to 17 hours when the level of biogenic amines in the meat accumulated to about 300 to 320 ppm respectively.

Figure 8:
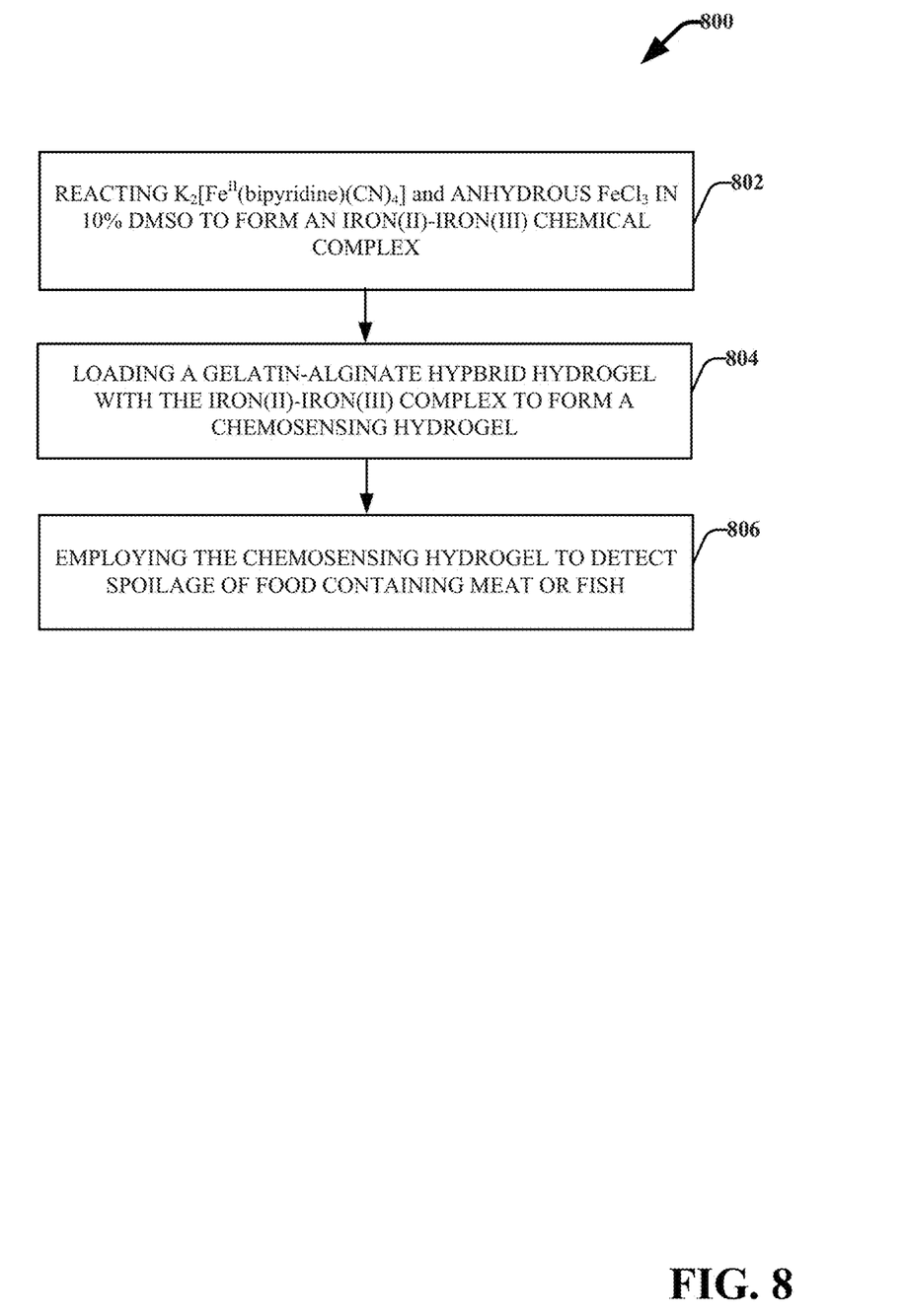
FIG. 8 presents a flow diagram of an example method for detecting food spoilage via a chemosensing hydrogel in accordance with various aspects and embodiments described herein.
Figure 9:
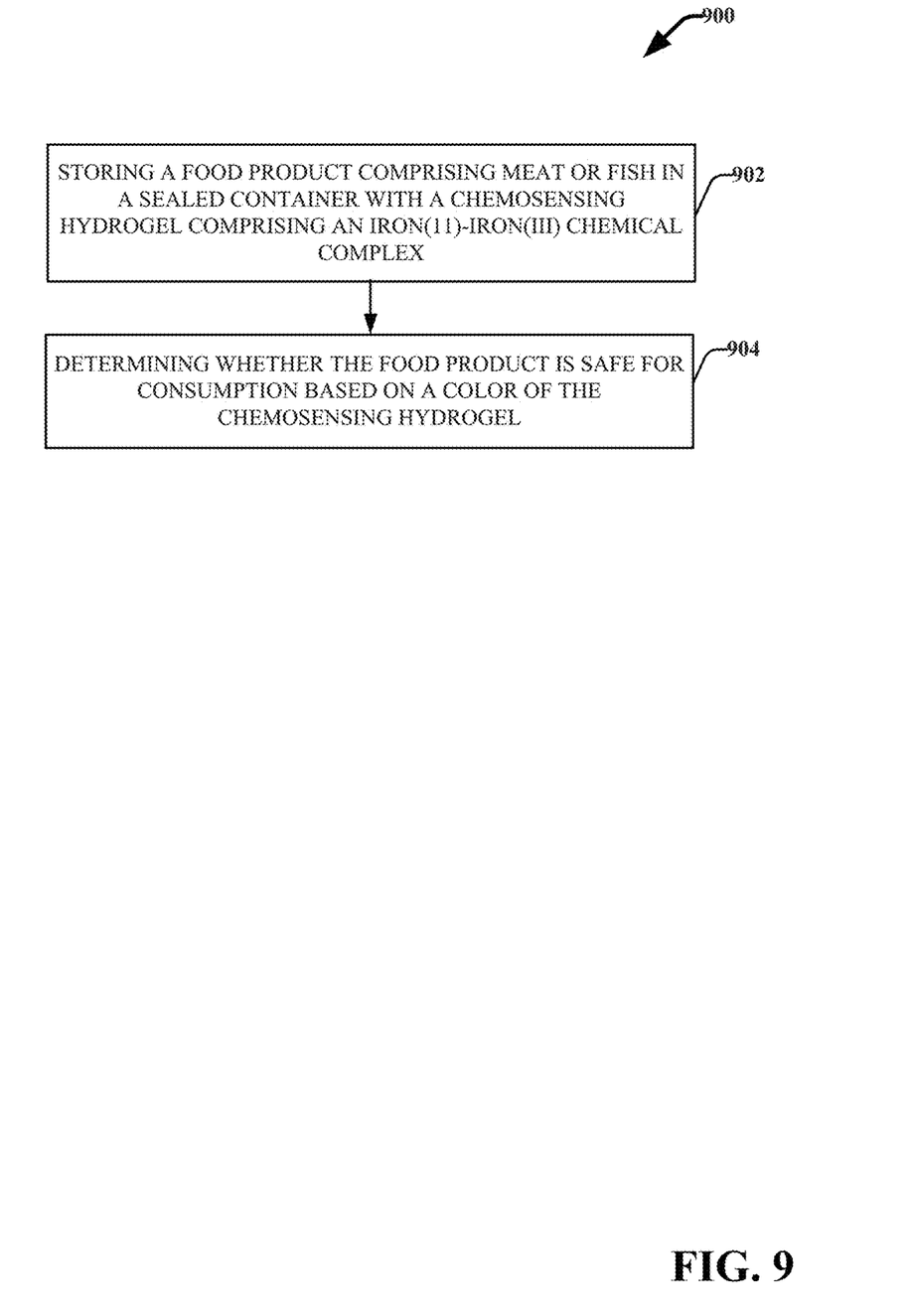
FIG. 9 presents a flow diagram of another example method for detecting food spoilage via a chemosensing hydrogel in accordance with various aspects and embodiments described herein.
Figure 10:
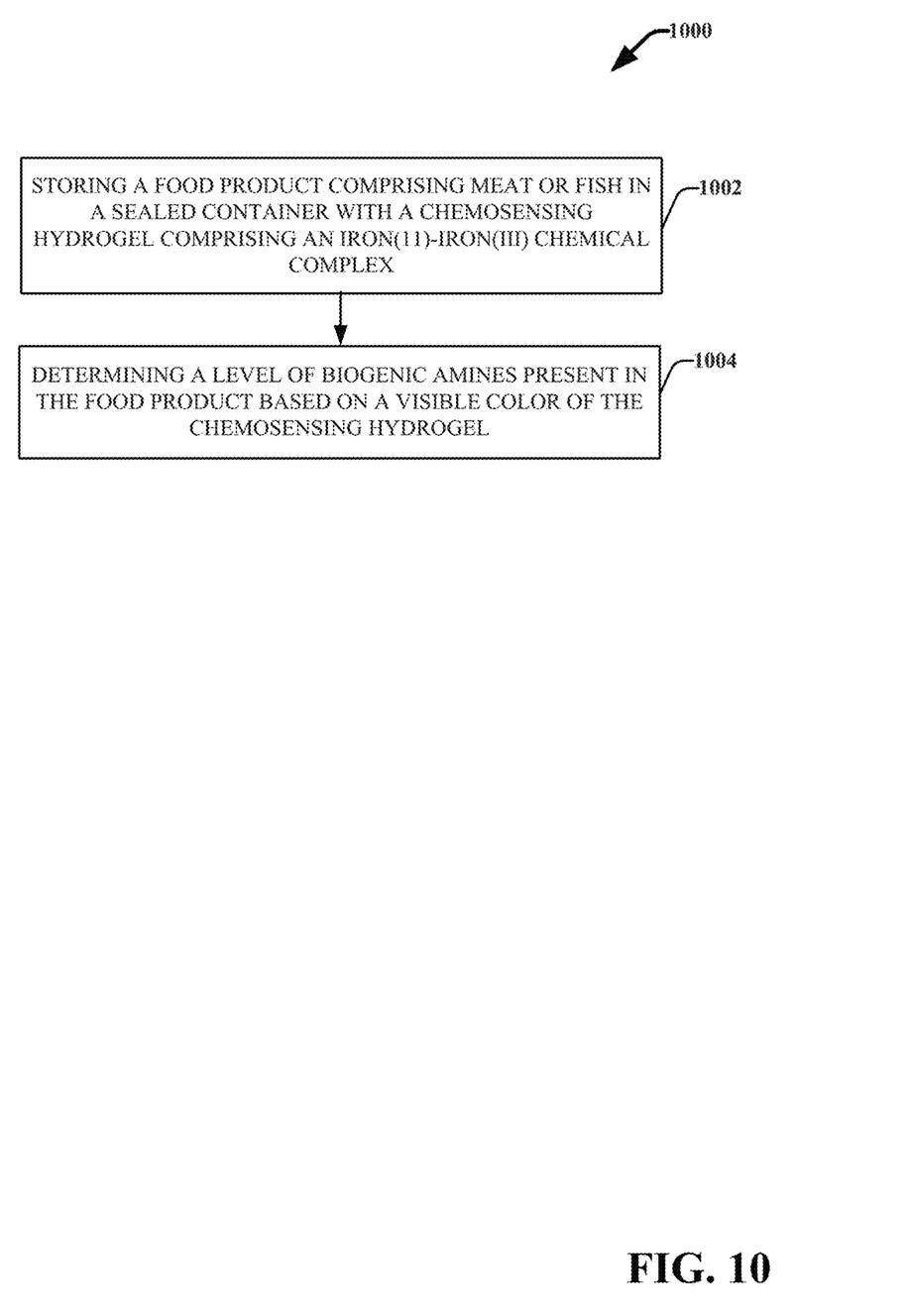
FIG. 10 presents a flow diagram of another example method for detecting food spoilage via a chemosensing hydrogel in accordance with various aspects and embodiments described herein.

In view of the example chemical complexes, hydrogels, and apparatuses described herein, example methods that can be implemented in accordance with the disclosed subject matter can be further appreciated with reference to flowcharts in FIGS. 8-10. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification.

FIG. 8 presents a flow diagram of an example method 800 for detecting food spoilage via a chemosensing hydrogel in accordance with various aspects and embodiments described herein. At 802, an iron(II)-iron(III) complex is synthesized by reacting $K_2[Fe^{II}$(bipyridine)(CN)$_4$] and anhydrous $FeCl_3$ in 10% aqueous DMSO. The resulting iron(II)-iron(III) complex has the chemical formula [$Fe^{II}$(bipyridine)(CN)$_4$]$_2$—[$Fe^{III}$(H$_2$O)$_6$Cl]$_2$}). At 804, a chemosensing hydrogel is formed by loading a gelatin-alginate hybrid hydrogel with the iron(II)-iron(III) complex. For example, the hydrogel can be soaked in a solution containing the iron(II)-iron(III) complex for about 8 hours. At 806, the chemosensing hydrogel is employed to detect the spoilage of food containing meat or fish.

FIG. 9 presents a flow diagram of another example method 900 for detecting food spoilage via a chemosensing hydrogel in accordance with various aspects and embodiments described herein. At 902, a food product comprising meat or fish is stored in a sealed container with a chemosensing hydrogel comprising an iron(II)-iron(III) complex. In an aspect, the iron(II)-iron(III) complex has the chemical formula [Fe$^{II}$(bipyridine)(CN)$_4$]$_2$—[Fe$^{III}$(H$_2$O)$_6$Cl]$_2$}). At 904, it is determined whether the food product is safe for consumption based on a color of the chemosensing hydrogel. For example, a red/orange color can indicate that the food product is spoiled and thus not safe for consumption while a green color can indicate the food product is not spoiled and safe for consumption.

FIG. 10 presents a flow diagram of another example method 1000 for detecting food spoilage via a chemosensing hydrogel in accordance with various aspects and embodiments described herein. At 1002, a food product comprising meat or fish is stored in a sealed container with a chemosensing hydrogel comprising an iron(II)-iron(III) complex. In an aspect, the iron(II)-iron(III) complex has the chemical formula [Fe$^{II}$(bipyridine)(CN)$_4$]$_2$—[Fe$^{III}$(H$_2$O)$_6$Cl]$_2$}). At 1004, a level of biogenic amines present in the food product is determined based on a color of the chemosensing hydrogel. For example, a red/orange color can indicate that the food product has more than N amount (e.g., 100 ppm) of biogenic amines, where N is a predetermined number.

What has been described above includes various example embodiments of a bimetallic iron(II)-iron(III) chemical complex for the detection of biogenic amines, a hydrogel including the complex, an apparatus for containing food including the hydrogel, and methods for detecting food spoilage via the hydrogel. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In this regard, with respect to any figure or numerical range for a given characteristic, a figure or a parameter from one range may be combined with another figure or a parameter from a different range for the same characteristic to generate a numerical range. Other than in the operating examples, or where otherwise indicated, all numbers, values and/or expressions referring to quantities of ingredients, reaction conditions, etc., used in the specification and claims are to be understood as modified in all instances by the term "about."

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A chemical complex for detection of biogenic amines, comprising a chemical structure of Structure I:

Structure I

2. The chemical complex of claim 1, wherein a solution comprising the chemical complex is configured to change from a first color to a second color in response to exposure to a biogenic amine.

3. The chemical complex of claim 2, wherein the biogenic amine comprises histamine, putrescine, spermidine, ammonia or tyramine.

4. The chemical complex of claim 2, wherein the first color is green and the second color is orange or red.

5. The chemical complex of claim 2, wherein the chemical structure comprises a cyano-bridge and wherein the cyano-bridge is configured to break in response to the exposure to the biogenic amine, thereby resulting in the change from the first color to the second color.

6. The chemical complex of claim 2, wherein the solution is synthesized from K$_2$[Fe$^{II}$(bipyridine)(CN)$_4$] and anhydrous FeCl$_3$ in 10% aqueous dimethyl sulfoxide (DMSO).

7. An apparatus for detection of biogenic amines, comprising:
a hydrogel; and
a bimetallic iron(II)-iron(III) complex disposed within the hydrogel, wherein the bimetallic iron(II)-iron(III) complex comprises a chemical structure of Structure I:

Structure I

8. The apparatus of claim 7, wherein the hydrogel is configured to change from a first color to a second color in response to exposure to a biogenic amine.

9. The apparatus of claim 7, wherein the bimetallic iron(II)-iron(III) complex comprises the chemical formula $[Fe^{II}(bipyridine)(CN)_4]_2$—$[Fe^{III}(H_2O)_6Cl]_2$.

10. The apparatus of claim 8, wherein the hydrogel is configured to change from the first color to the second color in response to exposure of a biogenic amine vapor.

11. The apparatus of claim 8, wherein the biogenic amine comprises histamine, putrescine, spermidine, ammonia or tyramine.

12. The apparatus of claim 8, wherein the first color is green and the second color is orange or red.

13. The apparatus of claim 8, wherein the bimetallic iron(II)-iron(III) complex comprises a cyano-bridge and wherein the cyano-bridge is configured to break in response to the exposure to the biogenic amine, thereby resulting in the change from the first color to the second color.

14. The apparatus of claim 7, wherein the hydrogel comprises alginate and gelatin.

15. The apparatus of claim 8, wherein the hydrogel is configured to change from the first color to the second color in response to exposure to the biogenic amine in the presence of moisture.

16. A package for the containment of a food product, comprising:
a hydrogel; and
a chemical complex disposed within the hydrogel for detection of biogenic amines, comprising a chemical structure of Structure I:

Structure I

17. The package of claim 16, wherein the chemical complex causes the hydrogel to change from a first color to a second color in response to exposure to a biogenic amine generated by the food product.

18. The package of claim 16, wherein the chemical complex comprises the chemical formula $[Fe^{II}(bipyridine)(CN)_4]_2$—$[Fe^{III}(H_2O)_6Cl]_2$.

19. The package of claim 17, wherein the hydrogel is configured to change from the first color to the second color in response to exposure of biogenic amine vapor generated by the food product.

20. The package of claim 16, wherein the package is configured to keep the food product physically separated from the hydrogel.

* * * * *